(12) United States Patent
Bjorge et al.

(10) Patent No.: US 10,597,622 B2
(45) Date of Patent: Mar. 24, 2020

(54) APPARATUS AND METHOD FOR HYDROLYSING A PRODUCT

(71) Applicant: FIRMENICH SA, Geneva (CH)

(72) Inventors: Ole Marius Bjorge, Ellingsoy (NO); Oddvar Bjorge, Ellingsoy (NO); Einar Lied, Bergen (NO)

(73) Assignee: Firmenich SA, Meyrin (CH)

( * ) Notice: Subject to any disclaimer, the term of this patent is extended or adjusted under 35 U.S.C. 154(b) by 210 days.

(21) Appl. No.: 15/531,996

(22) PCT Filed: Oct. 19, 2015

(86) PCT No.: PCT/EP2015/074134
§ 371 (c)(1),
(2) Date: May 31, 2017

(87) PCT Pub. No.: WO2016/066463
PCT Pub. Date: May 6, 2016

(65) Prior Publication Data
US 2018/0163163 A1 Jun. 14, 2018

(30) Foreign Application Priority Data

Oct. 27, 2014 (EP) ..................... 1419096

(51) Int. Cl.
| | | |
|---|---|---|
| *C12M 1/02* | (2006.01) | |
| *C12P 19/14* | (2006.01) | |
| *C12M 1/40* | (2006.01) | |
| *A23L 17/00* | (2016.01) | |
| *C12M 1/12* | (2006.01) | |
| *C12M 3/04* | (2006.01) | |
| *A23J 1/04* | (2006.01) | |
| *C12M 1/00* | (2006.01) | |
| *C12M 1/06* | (2006.01) | |

(52) U.S. Cl.
CPC ............... *C12M 21/18* (2013.01); *A23J 1/04* (2013.01); *A23L 17/65* (2016.08); *C12M 23/06* (2013.01); *C12M 23/52* (2013.01); *C12M 27/06* (2013.01); *C12M 27/10* (2013.01); *C12M 41/22* (2013.01); *C12Y 304/21014* (2013.01); *C12P 19/14* (2013.01)

(58) Field of Classification Search
CPC ...... C12M 21/18; C12M 23/06; C12M 23/10; C12M 41/22; C12P 19/14
See application file for complete search history.

(56) References Cited

U.S. PATENT DOCUMENTS 2,715,795 A * 8/1955 Pallotta .................. A01G 33/00
210/321.78

FOREIGN PATENT DOCUMENTS

DE 102009016738 A1 * 10/2010 ............ C12M 21/02

* cited by examiner

*Primary Examiner* — William H. Beisner
(74) *Attorney, Agent, or Firm* — Robert S. Dailey

(57) ABSTRACT

An apparatus for hydrolysing a product, comprising a continuous conduit having an inlet for receiving the product and an outlet for discharging the product, the conduit being formed so as to follow a path that winds around a longitudinal axis as the conduit extends parallel to the longitudinal axis between the inlet and the outlet, and a heating system for heating at least part of the conduit. The conduit is rotatable about the longitudinal axis so as to transport product received in the inlet towards the outlet.

15 Claims, 2 Drawing Sheets

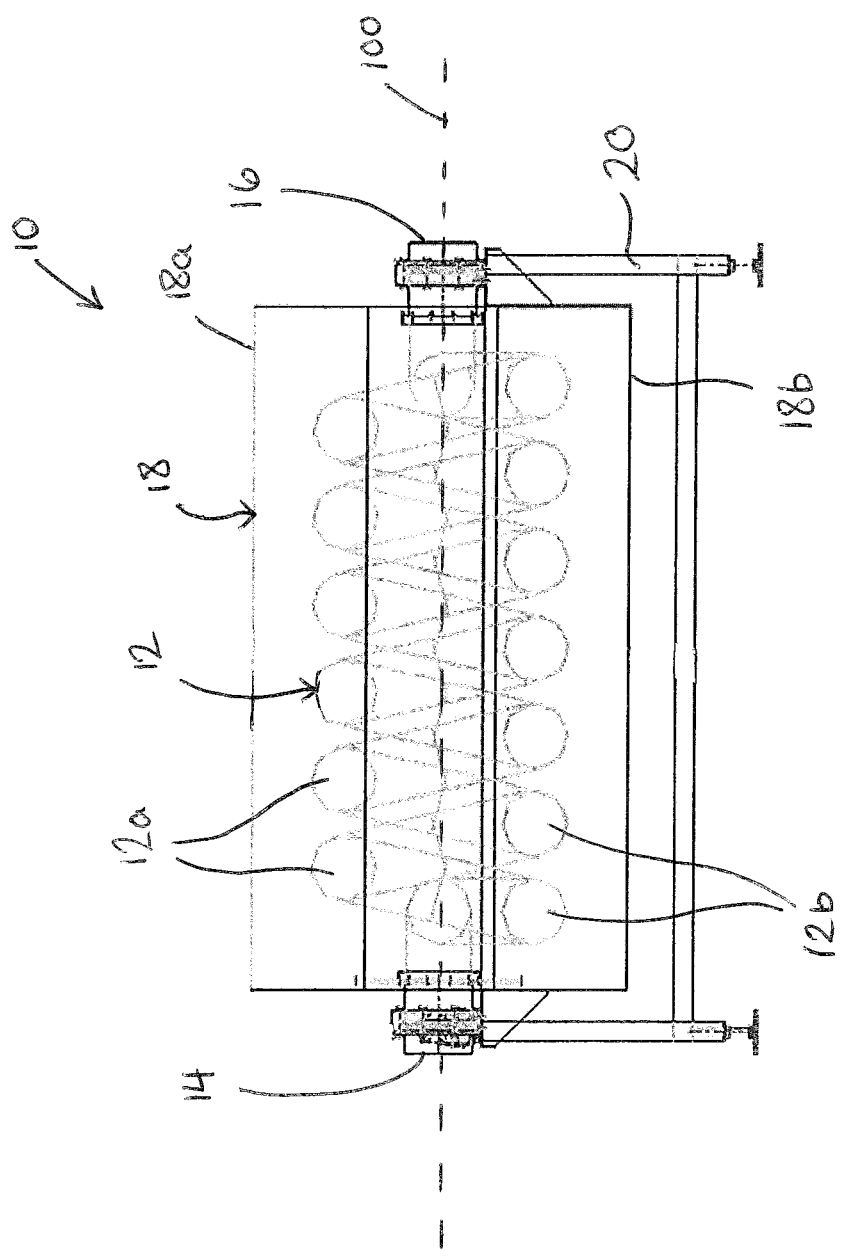

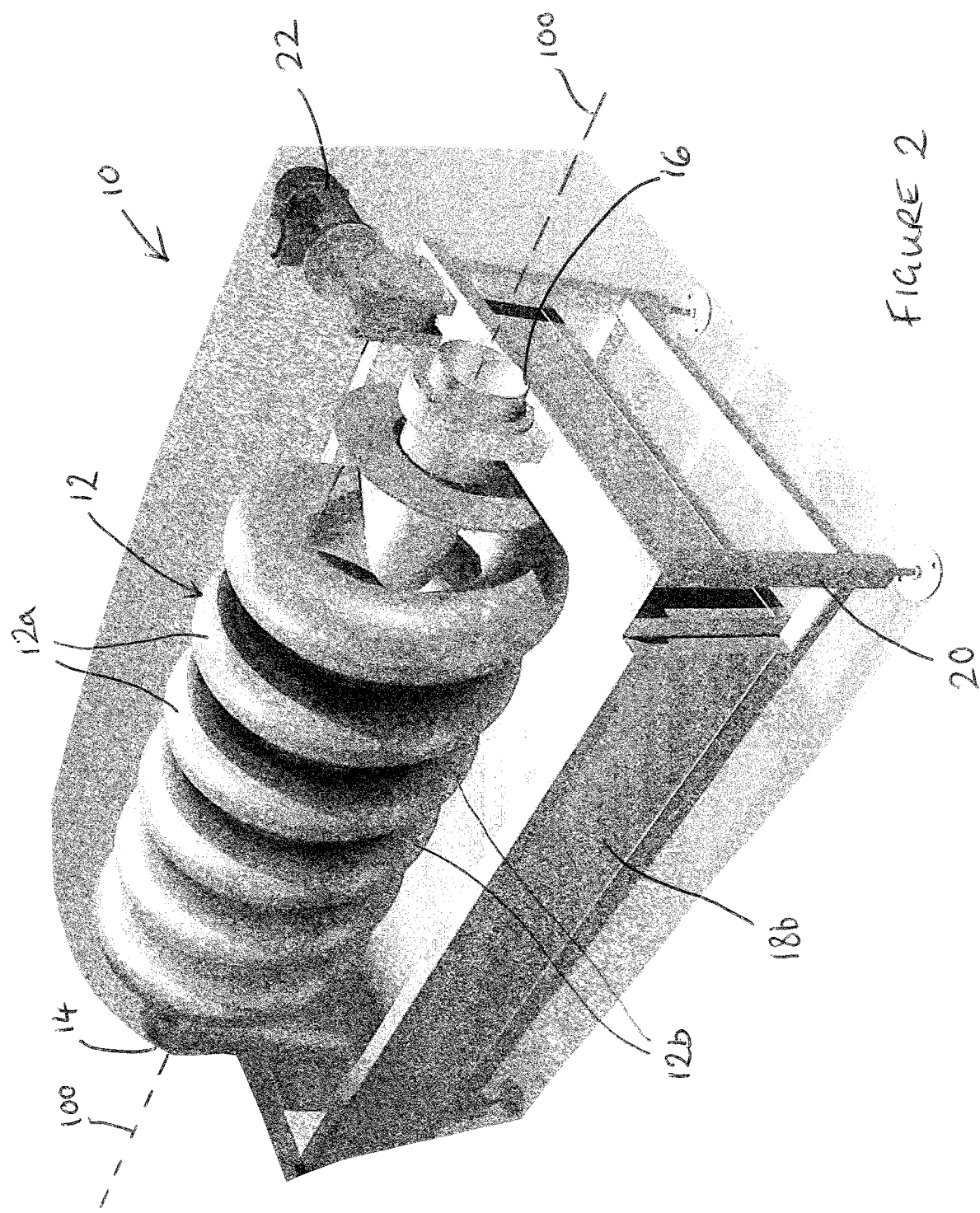

APPARATUS AND METHOD FOR HYDROLYSING A PRODUCT

BACKGROUND

The process of hydrolysation involves the chemical reaction of a compound with water and usually results in the formation of one or more new compounds. Hydrolysation may be used to extract certain compounds from a base material.

As an example, hydrolysation is used to extract or obtain certain compounds from seafood including fish meat and seafood by-products. Current known methods of hydrolysing products include batch processing wherein a product is deposited in a large tank for the duration of the hydrolysation process and retrieved therefrom thereafter.

There exists a need for an improved apparatus and/or method for hydrolysing a product.

Certain embodiments of the present invention seek to overcome one or more disadvantages associated with the prior art.

BRIEF SUMMARY OF THE DISCLOSURE

In accordance with an aspect of the present invention there is provided an apparatus for hydrolysing a product, comprising:

a continuous conduit having an inlet for receiving the product and an outlet for discharging the product, the conduit being formed so as to follow a path that winds around a longitudinal axis as the conduit extends parallel to the longitudinal axis between the inlet and the outlet; and a heating system for heating at least part of the conduit;

wherein the conduit is rotatable about the longitudinal axis so as to transport product received in the inlet towards the outlet.

The heating system may include a tank surrounding at least part of the conduit, wherein the tank is configured for containing a heated fluid so as to heat the conduit. The tank may further include a heater for heating fluid contained in the tank. Alternatively, the tank may be configured to receive a heated fluid.

The tank may include a bottom section and a top section, wherein the top section is moveable relative to the bottom section between a closed configuration in which the bottom and top sections form a closed chamber, and an open configuration in which the bottom and top sections do not form a closed chamber.

The apparatus may further comprise a driver for rotating the conduit so as to transport product received in the inlet towards the outlet. The driver may comprise a motor rotatably coupled to the conduit.

In certain embodiments, the conduit may be helical over at least a portion of its length.

The apparatus may further comprise a pump for introducing the product into the inlet.

In accordance with another aspect of the present invention there is provided a vehicle including the apparatus defined above. In one example, the vehicle is a watercraft.

In accordance with another aspect of the present invention there is provided a method of using the apparatus defined above, comprising:

providing an apparatus as defined above;

providing in the conduit a product-enzyme mixture that includes a product to be hydrolysed and one or more enzymes;

heating at least part of the conduit using the heating system; and rotating the conduit about the longitudinal axis so as to transport the product-enzyme mixture towards the outlet of the conduit.

The step of rotating the conduit about the longitudinal axis may optionally be performed at a rate such that the product-enzyme mixture is in the conduit for between 30 and 60 minutes, optionally between 40 and 50 minutes, and optionally about 45 minutes, before exiting the outlet of the conduit.

The step of heating at least part of the conduit using the heating system may optionally be performed so as to heat or maintain the product-enzyme mixture at a temperature of between 40 and 70° C., optionally between 50 and 60° C., and optionally about 55° C.

The step of rotating the conduit about the longitudinal axis may include rotating the conduit in a forward direction so as to transport the product-enzyme mixture towards the outlet of the conduit and rotating the conduit in a backward direction so as to transport the product-enzyme mixture away from the outlet of the conduit, wherein over a predetermined period of time the conduit is rotated in the forward direction by a greater amount relative to the backward direction so as to cause a net movement of the product-enzyme mixture towards the outlet.

In certain embodiments, the product to be hydrolysed is or includes seafood.

In certain embodiments, the one or more enzymes includes one or both of protease and alcalase.

The one or more enzymes form below 10% by mass, optionally below 5% by mass, and optionally below 1% by mass, of the total product-enzyme mixture.

BRIEF DESCRIPTION OF THE DRAWINGS

Embodiments of the invention are further described hereinafter with reference to the accompanying drawings, in which:

FIG. 1 is a cross-sectional side view of an apparatus in accordance with an embodiment of the present invention; and FIG. 2 is a perspective view of an apparatus in accordance with an embodiment of the present invention.

DETAILED DESCRIPTION

An apparatus 10 in accordance with an embodiment of the present invention is shown in FIG. 1. The apparatus 10 is suitable for hydrolysing a product, and, advantageously, may facilitate the continuous hydrolysation of product from a product supply.

The apparatus 10 includes a continuous conduit 12 that extends between an inlet 14 and an outlet 16. In the non-limiting embodiment shown in the Figures, the conduit 12 extends generally along a longitudinal axis 100 and is formed as a helix over the majority of its length between the inlet 14 and outlet 16. In alternative embodiments, the conduit 12 may be formed in other configurations in which the conduit 12 follows a path that winds around the longitudinal axis 100 as the conduit 12 extends parallel to the longitudinal axis 100 between the inlet 14 and the outlet 16. For example, the conduit may be formed of many straight sections that satisfy this definition.

Returning to the embodiment shown in the Figures, in cross-section (as shown in FIG. 1), the conduit 12 defines a series of peaks 12a above the longitudinal axis and a series of troughs 12b below the longitudinal axis.

The apparatus 10 further includes a frame 20 and a tank 18 mounted on the frame 20. The conduit 12 traverses the tank 18 along the longitudinal axis 100 and the conduit 12 is rotatably mounted in the tank 18 (e.g. by a rotation coupler and glider bearing). In particular, the conduit 12 is rotatably mounted such that the conduit 12 may rotate about the longitudinal axis 100. Rotation of the conduit 12 about the longitudinal axis 100 causes any product contained in the conduit 12 to translate within the conduit 12 along a direction parallel to the longitudinal axis 100. The direction of this translation (i.e. either away from or towards the outlet 16) will depend on the direction of rotation of the conduit 12 about the longitudinal axis 100. The apparatus 10 may additionally include a driver for rotating the conduit 12 about the longitudinal axis 100. The driver may comprise a motor 22 which is shown in FIG. 2. The motor 22, or, indeed, other driver, may be drivably coupled to the conduit 12 so as to cause rotation of the conduit 12. Examples of suitable drivable couplings include, but are not limited to, pulleys, chains and splined or otherwise geared connections.

The tank 18 includes a top section 18a and a bottom section 18b. FIG. 1 shows the tank 18 in a closed configuration in which the top section 18a is arranged relative to the bottom section 18b so as to form a closed chamber. Conversely, FIG. 2 shows the tank 18 in an open configuration in which the top section 18a has been removed from the bottom section 18b. The top section 18a is preferably moveable relative to the bottom section 18b so as to change the tank 18 between the closed configuration and open configuration.

In alternative embodiments, the tank 18 may include a single component, or multiple components that may or may not be moveable relative to one another. In any embodiment including a tank 18, the tank 18 may be configured for containing a heated fluid (which may be a liquid and/or a gas) so as to heat the conduit. For example, the tank 18 may be configured to receive and contain an already heated fluid, or it may include heating means in the form of a heater that is arranged to heat a fluid in the tank 18. The tank 18 may include one or more ports for receiving and/or expelling fluid or fluid may be introduced into the tank 18 when in an open configuration. Suitable fluids include water, air and steam. The tank 18 permits the temperature of the fluid (and hence the temperature of the conduit 12 and product) to be controlled and maintained as necessary.

In alternative embodiments, the apparatus 10 may not include a tank 18 at all. In such embodiments, heating of the conduit 12 may be achieved by a different heating system. Examples of alternative heating systems that may be used with certain embodiments of the present invention include, but are not limited to, induction coils, infrared heaters and heat pipes carrying heated fluid.

Optionally, the apparatus 10 may include one or more pumps or other propulsion mechanisms for introducing product into the inlet 14.

In use, product is introduced into the conduit 12 via the inlet 14 and the conduit 12 is rotated and heated. Rotation of the conduit 12 results in the product moving towards the outlet 16. If a continuous supply of product is provided to the inlet 14, the apparatus 10 may facilitate a continuous process where product may simultaneously enter the inlet 14 and exit the outlet 16.

In certain preferable embodiments, the product may be or contains seafood which may include fresh or frozen fish meat and/or seafood by-products. In certain embodiments, the aim may be to hydrolyse the proteins of the seafood product.

For hydrolysation, one or more enzymes are added to the product to form an enzyme-product mixture. The enzyme-product mixture may then be transported along the conduit 12 and simultaneously heated. The one or more enzymes may include protease and/or alcalase. The one or more enzymes may be added to the product prior to introduction into the conduit 12 or they may be added separately. The amount of enzymes used relative to the product to be hydrolysed will depend on the desired degree of hydrolysation and the speed of the hydrolysation process to be adopted. In certain preferable embodiments, the one or more enzymes may form below 10% by mass, optionally below 5% by mass, and optionally below 1% by mass, of the total product-enzyme mixture.

Prior to adding the enzymes, the water may be added to the product and the product (with water) may be heated (e.g. to around 50° C.). The amount of water added may depend on several factors including the desired degree of hydrolysation, and the consistency of the product to be hydrolysed. In certain embodiments, the added water may be between 20% and 200% of the mass of the product to which it is being added, and may optionally be between 30% and 100%. In one example water is added to the product to be hydrolysed where the water has a mass that is 30% of the product mass.

The product may be minced or otherwise processed prior to the one or more enzymes and/or water being added.

The conduit 12 may be rotated about the longitudinal axis at a rate such that the product-enzyme mixture is in the conduit 12 for between 30 and 60 minutes, optionally between 40 and 50 minutes, and optionally about 45 minutes, before exiting the outlet 16 of the conduit 12. The rate of rotation required for a particular product transit time will, at least in part, depend on the dimensions of the conduit 12. In certain preferable embodiments, the conduit 12 has a diameter between 150 mm and 300 mm, and preferably around 200 mm. In certain other embodiments, the conduit 12 may have a diameter up to 1000 mm. The axial length of the conduit 12 (i.e. the extent of the conduit in a direction parallel to the longitudinal axis 100) may, in certain embodiments, be between 1 m and 5 m. In a particularly preferable embodiment, the axial length of the conduit 12 is around 2 m. In certain preferable embodiments, the dimensions of the conduit 12 and the chosen rate of rotation of the conduit 12 result in a flow rate of product through the conduit 12 of between 150 and 350 L/h, and preferably around 250 L/h.

Rotation of the conduit 12 not only results in translation of the product along the conduit, but also results in agitation of the product-enzyme mixture which assists the hydrolysation process.

The conduit 12 may be rotated such that the rotation occurs in a forward direction so as to transport the product-enzyme mixture towards the outlet 16 and additionally in a backward direction so as to transport the product-enzyme mixture away from the outlet 16 of the conduit, wherein over a predetermined period of time the conduit 12 is rotated in the forward direction by a greater amount relative to the backward direction so as to cause a net movement of the product-enzyme mixture towards the outlet 16. By rotating serially in the forward and backward directions, the product contained in the conduit 12 is subject to greater agitation and this may further assist or enhance the hydrolysation.

Once the product-enzyme mixture is removed from the conduit 12 (e.g. by passing out of the outlet 16), the product-enzyme mixture may be subjected to heating to inactivate the enzymatic process (e.g. heated to around 90° C. for around 15 minutes).

If the product-enzyme mixture exiting the conduit 12 contains undesired impurities and/or solids (e.g. bones), certain purification processes (e.g. filtering or decanting) may be used to remove or reduce the impurities. The purification processes may be performed prior to or after the step of heating to inactivate the enzymatic process.

Water may be evaporated from the hydrolysed product to achieve a desired viscosity. Additionally or alternatively, the final hydrolysed product may be spray dried if required.

Certain embodiments of the present invention provide an apparatus for performing hydrolysation, wherein the apparatus may be relatively compact. In particular, the form of the conduit 12 permit a compact arrangement in comparison with prior art hydrolysation systems. Certain embodiments of the present invention provide an apparatus that may facilitate continuous hydrolysation of a product, provided an adequate supply is present. Certain embodiments of the present invention advantageously permit the hydrolysation process to take place at relatively low temperatures and permit the product to be maintained at a certain temperature throughout the process. Given the advantages associated with certain embodiments of the present invention, apparatus according to certain embodiments of the present invention may be particularly suitable for use on a vehicle such that the hydrolysation process can be performed in transit, possibly with the product or a product related to the one to be hydrolysed on board. As an example, apparatus according to certain embodiments of the present invention may be used on watercraft (e.g. fishing vessels) thereby facilitating the hydrolysation of seafood products close to the source of the products whilst negating the requirement of freezing and transporting the products to shore and hydrolysing the products at a land based site. In alternative embodiments, the apparatus may be used on other vehicles, such as land-based automobiles.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of hydrolyzing a product, the method comprising:
   (a) providing an apparatus, wherein the apparatus comprises:
      (a1) a continuous conduit having an inlet for receiving an initial product and an outlet for discharging a final product, wherein the conduit is formed so as to follow a path that winds around a longitudinal axis as the conduit extends parallel to the longitudinal axis between the inlet and the outlet, and wherein the conduit is rotatable about the longitudinal axis so as to transport initial product received in the inlet towards the outlet; and
      (a2) a heating system for heating at least part of the conduit;
   (b) introducing into the conduit via the inlet the initial product, wherein the initial product comprises a product-enzyme mixture that includes a product to be hydrolyzed and one or more enzymes;
   (c) heating at least part of the conduit using the heating system to hydrolyze the product-enzyme mixture and form the hydrolyzed product; and
   (d) rotating the conduit about the longitudinal axis so as to transport the hydrolyzed product mixture towards the outlet of the conduit.

2. The method of claim 1, wherein the rotating step is carried out for between 30 and 60 minutes before the hydrolyzed product exits the outlet of the conduit.

3. The method of claim 1, wherein the heating step is carried out at a temperature of between 40 and 70° C.

4. The method of claim 1, wherein the rotating step comprises rotating the conduit in a forward direction and rotating the conduit in a backward direction, wherein over a predetermined period of time the conduit is rotated in the forward direction by a greater amount relative to the backward direction.

5. The method of claim 1, wherein the product to be hydrolyzed comprises seafood.

6. The method of claim 1, wherein the one or more enzymes comprises a protease, an alcalase, or a combination thereof.

7. The method of claim 1, wherein the one or more enzymes form below 10% by mass of the initial product.

8. The method of claim 1, wherein the heating system includes a tank surrounding at least part of the conduit, wherein the tank is configured for containing a heated fluid so as to heat the conduit.

9. The method of claim 8, wherein the tank further includes a heater for heating fluid contained in the tank.

10. The method of claim 8, wherein the tank is configured to receive a heated fluid.

11. The method of claim 8, wherein the tank includes a bottom section and a top section, wherein the top section is moveable relative to the bottom section between a closed configuration in which the bottom and top sections form a closed chamber, and an open configuration in which the bottom and top sections do not form a closed chamber.

12. The method of claim 1, wherein the apparatus further comprises a driver for rotating the conduit so as to transport product received in the inlet towards the outlet.

13. The method of claim 12, wherein the driver comprises a motor rotatably coupled to the conduit.

14. The method of claim 1, wherein the conduit is helical over at least a portion of its length.

15. The method of claim 1, further comprising a pump for introducing the product into the inlet.

* * * * *